(12) United States Patent
Liang et al.

(10) Patent No.: US 9,033,878 B2
(45) Date of Patent: May 19, 2015

(54) GLUCOSE SENSOR SIGNAL RELIABILITY ANALYSIS

(75) Inventors: Bradley Liang, Bloomfield, MI (US); Kenneth W. Cooper, Newhall, CA (US); Raghavendhar Gautham, Los Angeles, CA (US); Rajiv Shah, Rancho Palos Verdes, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 624 days.

(21) Appl. No.: 13/282,228

(22) Filed: Oct. 26, 2011

(65) Prior Publication Data

US 2012/0108935 A1    May 3, 2012

Related U.S. Application Data

(60) Provisional application No. 61/407,884, filed on Oct. 28, 2010.

(51) Int. Cl.
| | |
|---|---|
| *G01N 21/00* | (2006.01) |
| *A61B 5/05* | (2006.01) |
| *A61B 5/145* | (2006.01) |
| *A61B 5/1486* | (2006.01) |
| *A61B 5/00* | (2006.01) |
| *A61M 5/142* | (2006.01) |
| *A61M 5/172* | (2006.01) |

(52) U.S. Cl.
CPC ......... *A61B 5/14532* (2013.01); *A61B 5/14865* (2013.01); *A61B 5/4839* (2013.01); *A61B 5/7221* (2013.01); *A61B 2560/0276* (2013.01); *A61M 5/14248* (2013.01); *A61M 5/1723* (2013.01); *A61M 2205/50* (2013.01); *A61M 2230/201* (2013.01); *A61B 5/6849* (2013.01)

(58) Field of Classification Search
USPC .......................................... 600/365
See application file for complete search history.

(56) References Cited

U.S. PATENT DOCUMENTS

| | | | |
|---|---|---|---|
| 2007/0016381 A1* | 1/2007 | Kamath et al. ................. | 702/19 |
| 2008/0183399 A1 | 7/2008 | Goode | |
| 2008/0249384 A1 | 10/2008 | Skyggebjerg | |
| 2009/0018418 A1 | 1/2009 | Markle | |
| 2009/0192380 A1 | 7/2009 | Shariati | |
| 2011/0270346 A1* | 11/2011 | Frei et al. ....................... | 607/45 |

OTHER PUBLICATIONS

U.S. Appl. No. 13/282,128, filed Oct. 26, 2011, 60 pages.
U.S. Appl. No. 13/282,128: Notice to file missing parts and filing receipt mailed Nov. 8, 2011, 6 pages.
U.S. Appl. No. 13/282,128: Response to notice to file missing parts mailed Feb. 1, 2012, 22 pages.
U.S. Appl. No. 13/282,128: Updated filing receipt mailed Feb. 10, 2012, 5 pages.
U.S. Appl. No. 13/282,128: Notice of publication, mailed May 24, 2012, 1 page.
U.S. Appl. No. 13/282,128: Non-final rejection, mailed Aug. 28, 2013, 15 pages.
U.S. Appl. No. 13/282,128: Office action response, mailed Dec. 5, 2013, 20 pages.

(Continued)

*Primary Examiner* — Michael Kahelin
*Assistant Examiner* — Mitchell E Alter
(74) *Attorney, Agent, or Firm* — Berkeley Law & Technology Group, LLP

(57) ABSTRACT

Disclosed are methods, apparatuses, etc. for glucose sensor signal reliability analysis.

7 Claims, 15 Drawing Sheets

(56) References Cited

OTHER PUBLICATIONS

U.S. Appl. No. 13/282,128: Final Office Action, mailed Mar. 26, 2014, 22 pages.

U.S. Appl. No. 13/282,128: Request for continued examination, mailed Jun. 12, 2014, 19 pages.

U.S. Appl. No. 13/282,128: Notice of allowance, mailed Aug. 13, 2014, 8 pages.

* cited by examiner

GLUCOSE SENSOR SIGNAL RELIABILITY ANALYSIS

This application claims the benefit of priority to U.S. Provisional Patent Application No. 61/407,884, titled "Glucose Sensor Reliability Analysis," filed on Oct. 28, 2010, and assigned to the assignee of claimed subject matter.

BACKGROUND

1. Field

Subject matter disclosed herein relates to glucose sensor signal reliability analysis.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, which is a condition known as Type I diabetes mellitus (or in some cases, if β-cells produce insufficient quantities of insulin, a condition known as Type II diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of the Type I diabetic individuals in the United States were using infusion pump therapy. Over time, greater than 7% of the more than 900,000 Type I diabetic individuals in the U.S. began using infusion pump therapy. The percentage of Type I diabetic individuals that use an infusion pump is now growing at a rate of over 2% each year. Moreover, the number of Type II diabetic individuals is growing at 3% or more per year, and increasing numbers of insulin-using Type II diabetic individuals are also adopting infusion pumps. Physicians have recognized that continuous infusion can provide greater control of a diabetic individual's condition, so they are increasingly prescribing it for patients.

A closed-loop infusion pump system may include an infusion pump that is automatically and/or semi-automatically controlled to infuse insulin into a patient. The infusion of insulin may be controlled to occur at times and/or in amounts that are based, for example, on blood glucose measurements obtained from an embedded blood-glucose sensor, e.g., in real-time. Closed-loop infusion pump systems may also employ the delivery of glucagon, in addition to the delivery of insulin, for controlling blood-glucose and/or insulin levels of a patient (e.g., in a hypoglycemic context). Glucagon delivery may also be based, for example, on blood glucose measurements that are obtained from an embedded blood-glucose sensor, e.g., in real-time.

SUMMARY

Briefly, example embodiments may relate to methods, systems, apparatuses, and/or articles, for analyzing the reliability of a glucose sensor signal. In one particular implementation, a method comprises: obtaining a plurality of glucose sensor measurements at a glucose sensor over a time interval; and detecting a change in responsiveness of said glucose sensor to a presence of glucose in a fluid based, at least in part, on an application of one or more thresholds to one or more sensitivity metrics, at least one of said sensitivity metrics being based, at least in part, on said glucose sensor measurements. In one example, the change in responsiveness comprises a decrease in sensitivity of the glucose sensor to the presence of glucose in said fluid. In another example, at least one of the sensitivity metrics comprises a measurement of dispersion of a rate change in said blood glucose sensor measurements over at least a portion of the time interval. For example, the measurement of dispersion of said rate of change may comprise a variance of the rate of change. In another example implementation, at least one of the sensitivity metrics comprises a computed mean value of said sensor measurements obtained over said portion of said time interval. In yet another example implementation, an alert signal is generated in response to the detected change in said responsiveness. In yet another example implementation, the portion of the time interval comprises a sliding time window. In yet another embodiment, the one or more sensitivity metrics comprise at least a measurement of dispersion of a rate change in the blood glucose sensor measurements and a mean value of the sensor measurements over at least a portion of the time interval, and wherein a decrease in sensitivity of the sensor is detected if the measurement of dispersion of a rate change in said blood glucose sensor measurements does not exceed a first threshold and the mean value of said sensor measurements does not exceed a second threshold. In another implementation, the fluid comprises interstitial fluid. In yet another implementation, detecting the change in responsiveness of the glucose sensor to the presence of glucose in the fluid further comprises: defining a sequence of windows in time; for at least one of said windows, computing a dispersion of said rate of change; and determining at least one of said sensitivity metrics based, at least in part, on said computed dispersion. In yet another implementation, determining the at least one of the sensitivity metrics further comprises determining the at least one of the sensitivity metrics based, at least in part, on a ratio of the computed dispersion and a mean value of glucose sensor measurements obtained in the at least one of said windows.

In another particular implementation, an apparatus comprises: a glucose sensor to obtain measurements responsive to a presence of glucose in a fluid; and a processor to: detect a change in responsiveness of said glucose sensor to the presence of glucose in the fluid based, at least in part, on an application of one or more thresholds to one or more sensitivity metrics, at least one of said sensitivity metrics being computed based, at least part, on the measurements. In a particular example implementation, the change in responsiveness comprises a decrease in sensitivity of said glucose to the presence of glucose in the fluid. In another implementation, at least one of the sensitivity metrics comprises a measurement of dispersion of a rate change in the blood glucose sensor measurements over at least a portion of the time interval. In another example implementation, the measurement of dispersion of the rate of change comprises a variance of the rate of change. In another implementation, the change in responsiveness of the glucose sensor to the presence of glucose in said fluid is detected by: defining a sequence of windows in time; for at least one of the windows, computing a dispersion of the rate of change; and determining at least one of the sensitivity metrics based, at least in part, on the computed dispersion. In yet another implementation, the at least one of the sensitivity metrics are detected by determining the at least one of the sensitivity metrics based, at least in part, on a ratio of said computed dispersion and a mean value of glucose sensor measurements obtained in the at least one of the windows.

In another particular implementation, an article comprises a non-transitory storage medium having machine-readable instructions stored thereon which are executable by a special purpose computing apparatus to: obtain a plurality of glucose sensor measurements at a glucose sensor over a time interval; and detect a change in responsiveness of the glucose sensor to a presence of glucose in a fluid based, at least in part, on an application of one or more thresholds to one or more sensitivity metrics, at least one of the sensitivity metrics being based, at least in part, on the glucose sensor measurements. In an example implementation, the change in responsiveness comprises a decrease in sensitivity of the glucose sensor to the presence of glucose in the fluid. In an example implementation, at least one of the sensitivity metrics comprises a measurement of dispersion of a rate change in the blood glucose sensor measurements over at least a portion of the time interval. In another implementation, the measurement of dispersion of the rate of change comprises a variance of the rate of change. In another example implementation, the change in responsiveness of the glucose sensor to the presence of glucose in said fluid is detected by: defining a sequence of windows in time; for at least one of said windows, computing a dispersion of the rate of change; and determining at least one of the sensitivity metrics based, at least in part, on the computed dispersion.

In yet another example implementation, an apparatus comprises: means for obtaining a plurality of glucose sensor measurements at a glucose sensor over a time interval; and means for detecting a change in responsiveness of said glucose sensor to a presence of glucose in a fluid based, at least in part, on an application of one or more thresholds to one or more sensitivity metrics, at least one of said sensitivity metrics being based, at least in part, on said glucose sensor measurements.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device/processor may be adapted to perform at least a portion of described method(s) according to one or more particular implementations based upon one or more signals generated by the sensor.

BRIEF DESCRIPTION OF THE FIGURES

Non-limiting and non-exhaustive features are described with reference to the following figures, wherein like reference numerals refer to like and/or analogous parts throughout the various figures.

DETAILED DESCRIPTION

Figure 1:
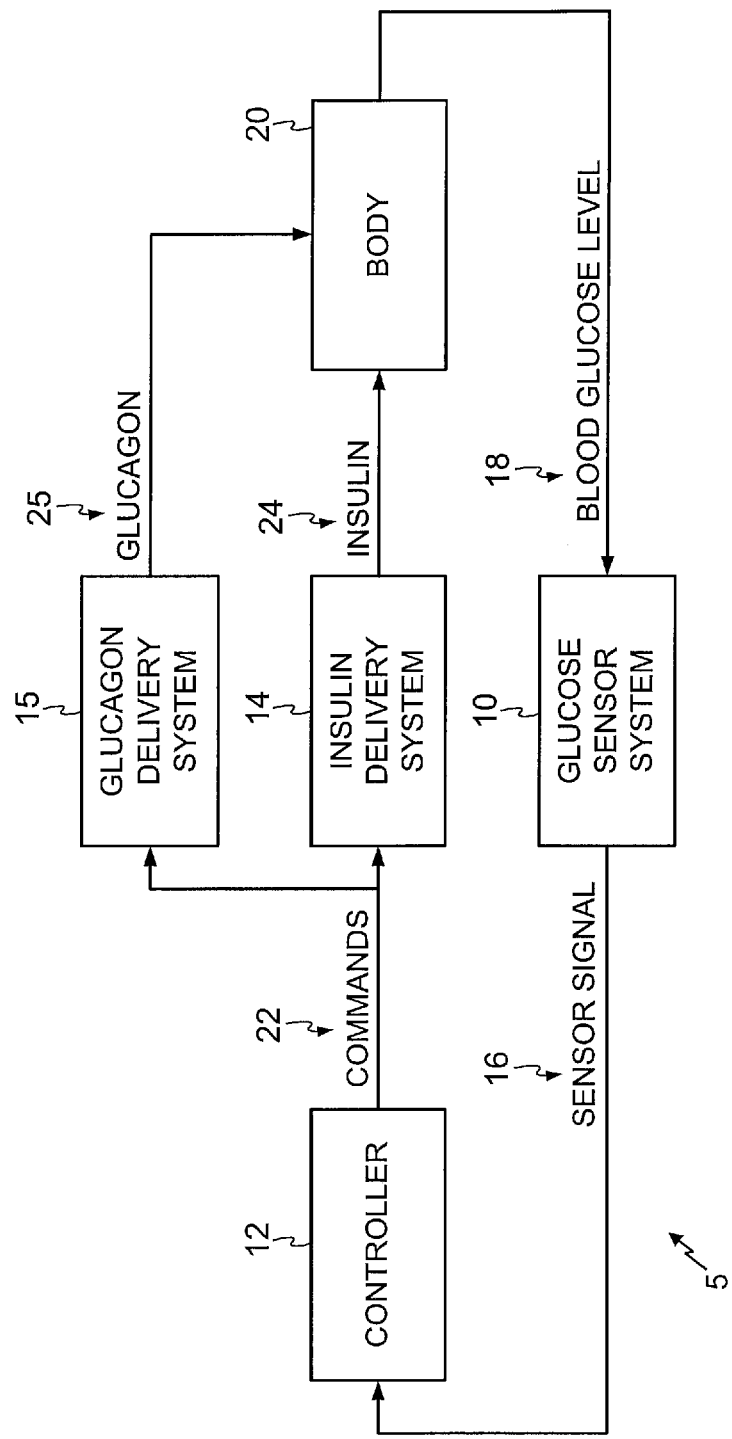
FIG. 1 is a schematic diagram of an example closed loop glucose control system in accordance with an embodiment.

In an example glucose monitoring sensor and/or insulin delivery system environment, measurements reflecting blood-glucose levels may be employed in a closed loop infusion system for regulating a rate of fluid infusion into a body. In particular example embodiments, a sensor and/or system may be adapted to regulate a rate of insulin and/or glucagon infusion into a body of a patient based, at least in part, on a glucose concentration measurement taken from a body (e.g., from a blood-glucose sensor, including a current sensor). In certain example implementations, such a system may be designed to model a pancreatic beta cell (β-cell). Here, such a system may control an infusion device to release insulin into a body of a patient in an at least approximately similar concentration profile as might be created by fully functioning human β-cells, if such were responding to changes in blood glucose concentrations in the body. Thus, such a closed loop infusion system may simulate a body's natural insulin response to blood glucose levels. Moreover, it may not only make efficient use of insulin, but it may also account for other bodily functions as well because insulin can have both metabolic and mitogenic effects.

According to certain embodiments, examples of closed-loop systems as described herein may be implemented in a hospital environment to monitor and/or control levels of glucose and/or insulin in a patient. Here, as part of a hospital or other medical facility procedure, a caretaker or attendant may be tasked with interacting with a closed-loop system to, for example: enter blood-glucose reference measurement samples into control equipment to calibrate blood glucose measurements obtained from blood-glucose sensors, make manual adjustments to devices, and/or make changes to therapies, just to name a few examples. Alternatively, according to certain embodiments, examples of closed-loop systems as described herein may be implemented in non-hospital environments to monitor and/or control levels of glucose and/or insulin in a patient. Here, a patient or other non-medical professional may be involved in interacting with a closed-loop system.

However, while a closed-loop glucose control system is active, oversight by medical professionals, patients, non-medical professionals, etc. is typically reduced. Such a closed-loop glucose control system may become at least partially responsible for the health, and possibly the survival, of a diabetic patient. To more accurately control blood glucose levels of a patient, a closed-loop system may be provided an observation of a current blood glucose level. One approach to providing such an observation is implementation of a blood glucose sensor, such as including one or more such glucose sensors in a closed-loop system.

A closed-loop system may receive at least one glucose sensor signal from one or more glucose sensors, with the glucose sensor signal intended to accurately represent a current (or at least relatively current) blood glucose level. If a glucose sensor signal indicates that a blood glucose level is currently too high, then a closed-loop system may take action(s) to lower the glucose level. On the other hand, if a glucose sensor signal indicates that a blood glucose level is currently too low, then a closed-loop system may take action(s) to raise the glucose level. Actions taken by a closed-loop system to control blood glucose levels of a patient and protect the patient's health may therefore be based at least partly on an accuracy and reliability of a glucose sensor signal received from a glucose sensor.

Unfortunately, a received glucose sensor signal may not be completely reliable as a representation of a current blood glucose level of a patient. For example, a glucose sensor may gradually become increasingly less capable of accurately measuring a current blood glucose level. In such situations, a glucose sensor signal that is received at a controller of a closed-loop system may not be sufficiently reliable to justify entrusting a patient's life and health to its control decisions.

In certain embodiments that are described herein, a closed loop system may assess a reliability of at least one sensor signal with respect to its ability to accurately reflect a blood glucose level of a patient. Among other things, a sensor may lose sensitivity to the presence of blood glucose over time as a sensor is worn on a patient. In one particular embodiment, a change in a sensor's sensitivity to blood-glucose concentration may be detected based, at least in part, at least in part, on an estimate of a dispersion of a rate change in blood glucose sensor measurements over a time interval. If such a sensitivity is determined to decrease significantly, the sensor may be repaired or replaced. In particular systems that employ multiple sensors, measurements from a sensor with diminished sensitivity may be discarded or de-weighted in computing an estimate of actual blood-glucose concentration. It should be understood, however, that this is merely an example embodiment and that claimed subject matter is not limited in this respect.

FIG. 1 is a block diagram of an example closed loop glucose control system 5 in accordance with an embodiment. Particular embodiments may include a glucose sensor system 10, a controller 12, an insulin delivery system 14, and a glucagon delivery system 15, etc. as shown in FIG. 1. In certain example embodiments, glucose sensor system 10 may generate a sensor signal 16 representative of blood glucose levels 18 in body 20, and glucose sensor system 10 may provide sensor signal 16 to controller 12. Controller 12 may receive sensor signal 16 and generate commands 22 that are communicated at least to insulin delivery system 14 and/or glucagon delivery system 15. Insulin delivery system 14 may receive commands 22 and infuse insulin 24 into body 20 in response to commands 22. Likewise, glucagon delivery system 15 may receive commands 22 from controller 12 and infuse glucagon 25 into body 20 in response to commands 22.

Glucose sensor system 10 may include, by way of example but not limitation, a glucose sensor; sensor electrical components to provide power to a glucose sensor and to generate sensor signal 16; a sensor communication system to carry sensor signal 16 to controller 12; a sensor system housing for holding, covering, and/or containing electrical components and a sensor communication system; any combination thereof, and so forth.

Figure 9:
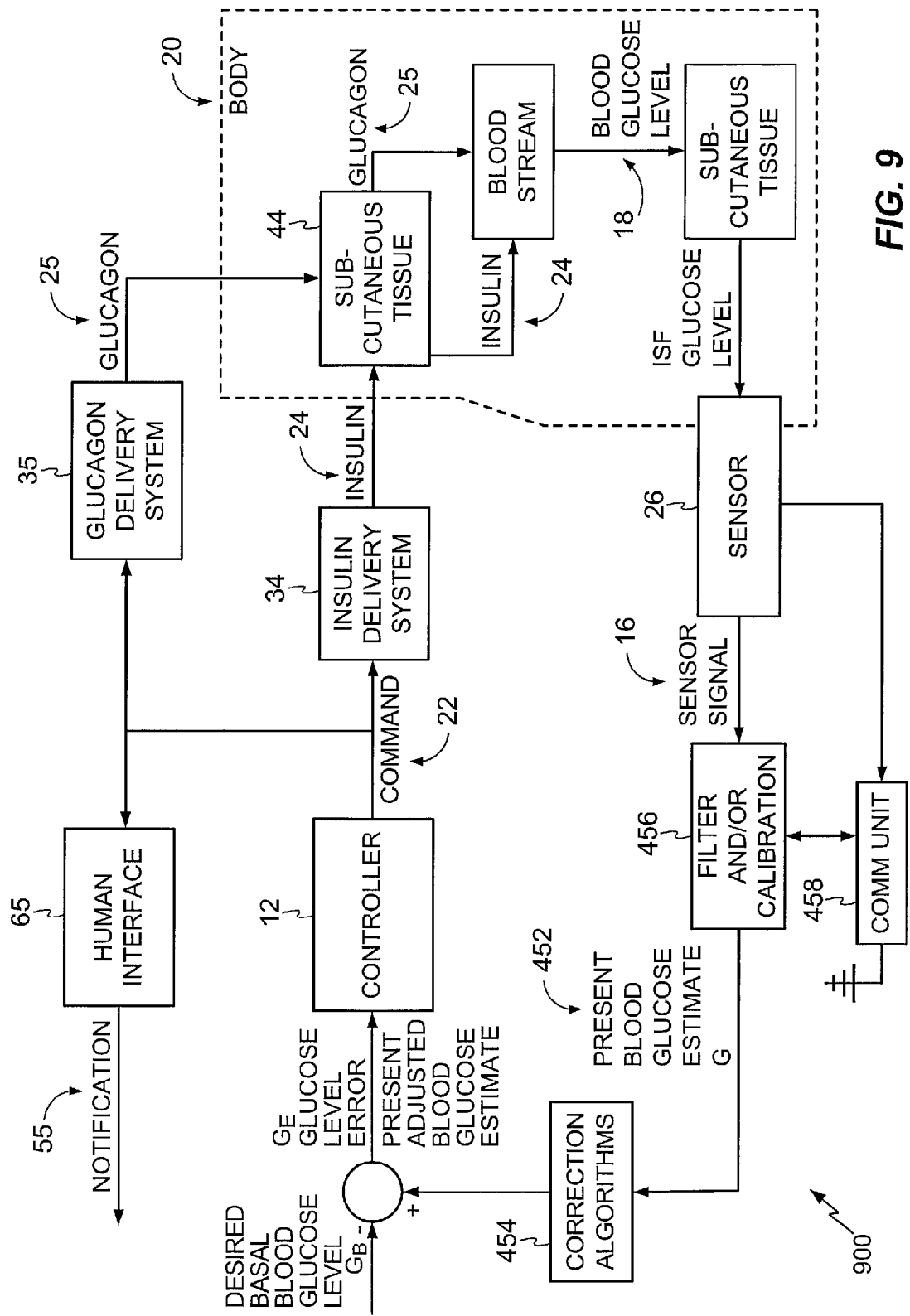
FIG. 9 is a schematic diagram of an example closed loop system to control blood glucose levels via insulin infusion and/or glucagon infusion using at least a controller based on glucose level feedback via a sensor signal in accordance with an embodiment.

Controller 12 may include, by way of example but not limitation, electrical components, other hardware, firmware, and/or software, etc. to generate commands 22 for insulin delivery system 14 and/or glucagon delivery system 15 based at least partly on sensor signal 16. Controller 12 may also include a controller communication system to receive sensor signal 16 and/or to provide commands 22 to insulin delivery system 14 and/or glucagon delivery system 15. In particular example implementations, controller 12 may include a user interface and/or operator interface (e.g., a human interface as shown in FIG. 9) comprising a data input device and/or a data output device. Such a data output device may, for example, generate signals to initiate an alarm and/or include a display or printer for showing a status of controller 12 and/or a patient's vital indicators, monitored historical data, combinations thereof, and so forth. Such a data input device may comprise dials, buttons, pointing devices, manual switches, alphanumeric keys, a touch-sensitive display, combinations thereof, and/or the like for receiving user and/or operator inputs. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 15 may include an infusion device and/or an infusion tube to infuse glucagon 25 into body 20. In alternative embodiments, insulin 24 and glucagon 25 may be infused into body 20 using a shared infusion tube.

In other alternative embodiments, insulin 24 and/or glucagon 25 may be infused using an intravenous system for providing fluids to a patient (e.g., in a hospital or other medical environment). When an intravenous system is employed, glucose may be infused directly into a bloodstream of a body instead of or in addition to infusing glucagon into interstitial tissue. It should also be understood that certain example embodiments for closed loop glucose control system 5 may include an insulin delivery system 14 without a glucagon delivery system 15 (or vice versa).

In particular example embodiments, an infusion device (not explicitly identified in FIG. 1) may include infusion electrical components to activate an infusion motor according to commands 22; an infusion communication system to receive commands 22 from controller 12; an infusion device housing (not shown) to hold, cover, and/or contain the infusion device; any combination thereof; and so forth.

In particular example embodiments, controller 12 may be housed in an infusion device housing, and an infusion communication system may comprise an electrical trace or a wire that carries commands 22 from controller 12 to an infusion device. In alternative embodiments, controller 12 may be housed in a sensor system housing, and a sensor communication system may comprise an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within one shared housing. In further alternative embodiments, a sensor, a controller, and/or infusion communication systems may utilize a cable; a wire; a fiber optic line; RF, IR, or ultrasonic transmitters and receivers; combinations thereof; and/or the like instead of electrical traces, just to name a few examples.

Overview of Example Systems

Figure 2:
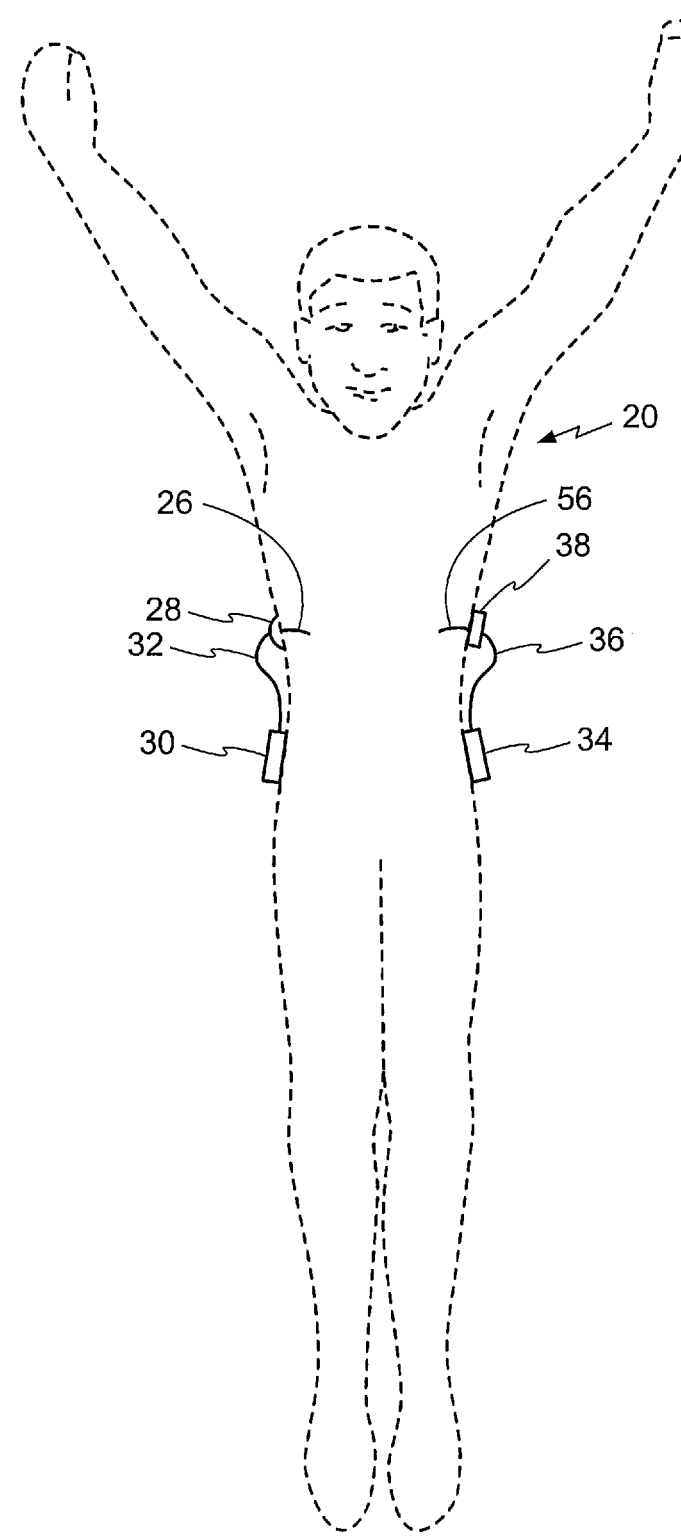
FIG. 2 is a front view of example closed loop hardware located on a body in accordance with an embodiment.
Figure 3:
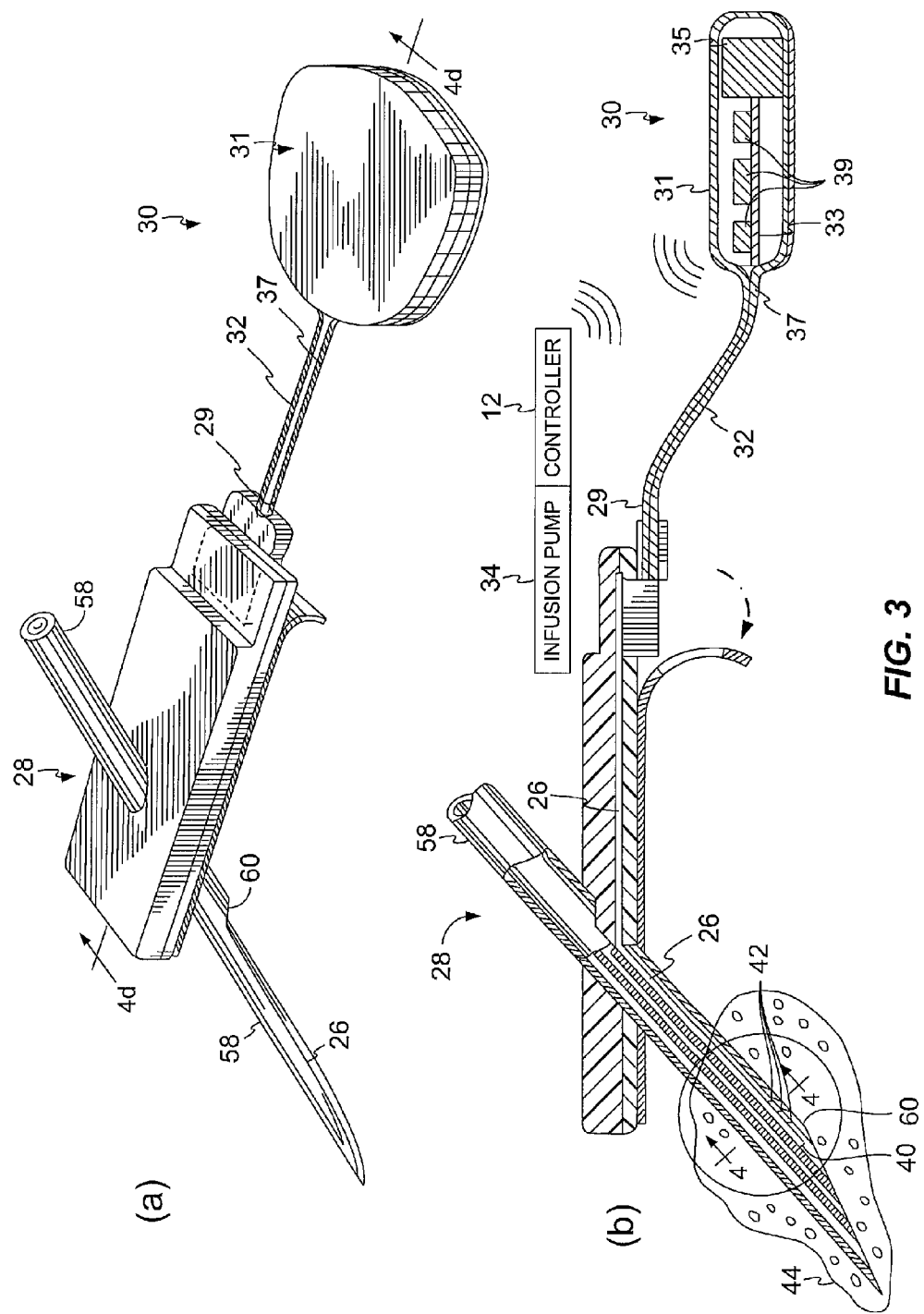
FIG. 3(a) is a perspective view of an example glucose sensor system for use in accordance with an embodiment.
FIG. 3(b) is a side cross-sectional view of a glucose sensor system of FIG. 3(a) for an embodiment.
FIG. 3(c) is a perspective view of an example sensor set for a glucose sensor system of FIG. 3(a) for use in accordance with an embodiment.
FIG. 3(d) is a side cross-sectional view of a sensor set of FIG. 3(c) for an embodiment.
Figure 3:
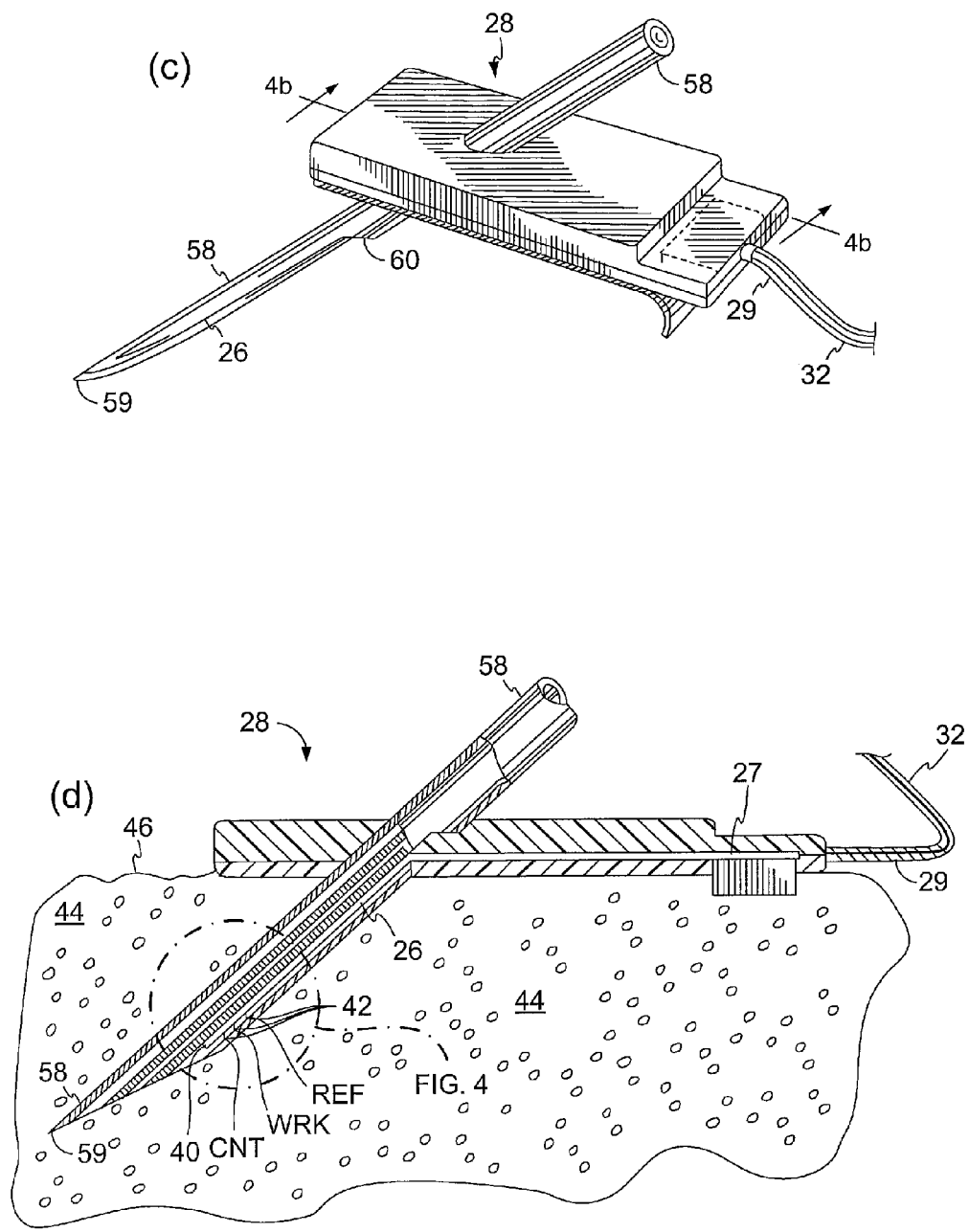
Figure 4:
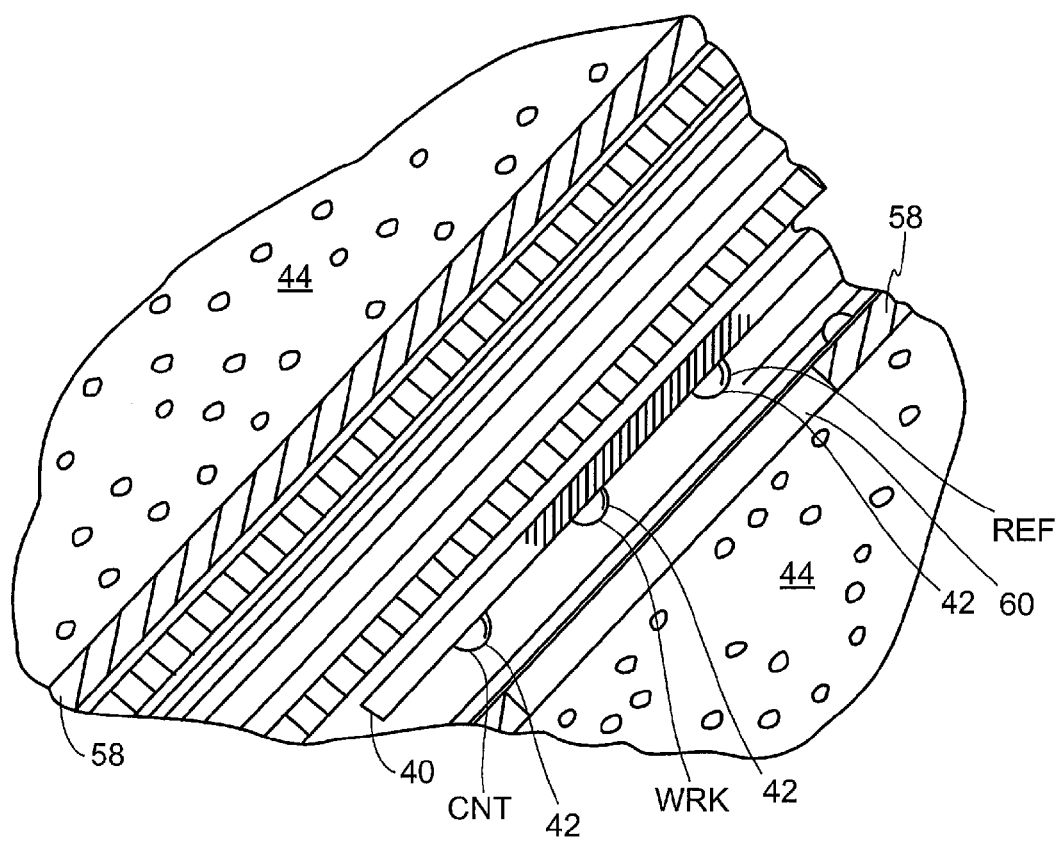
FIG. 4 is a cross sectional view of an example sensing end of a sensor set of FIG. 3(d) for use in accordance with an embodiment.
Figure 5:
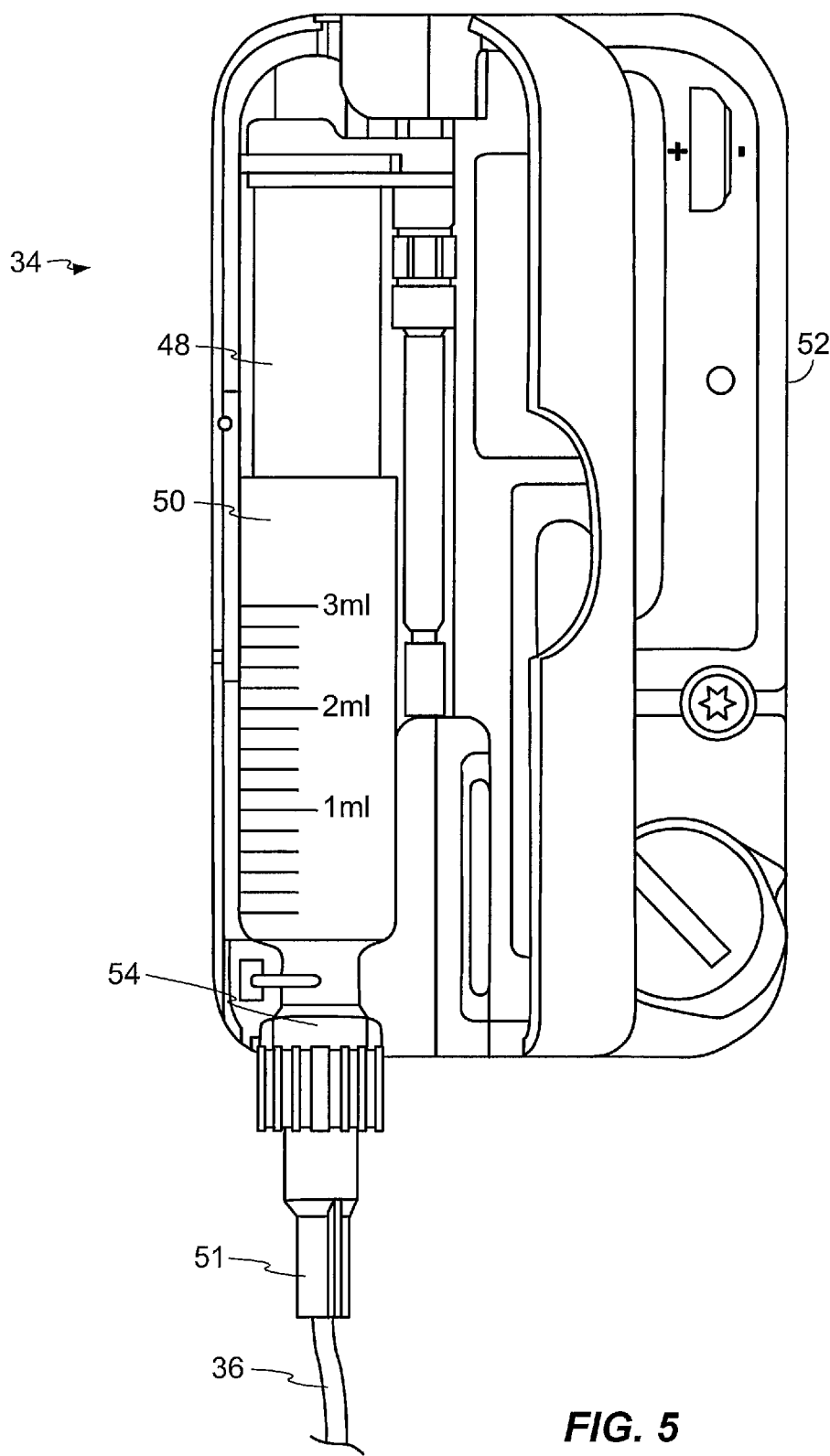
FIG. 5 is a top view of an example infusion device with a reservoir door in an open position, for use according to an embodiment.
Figure 6:
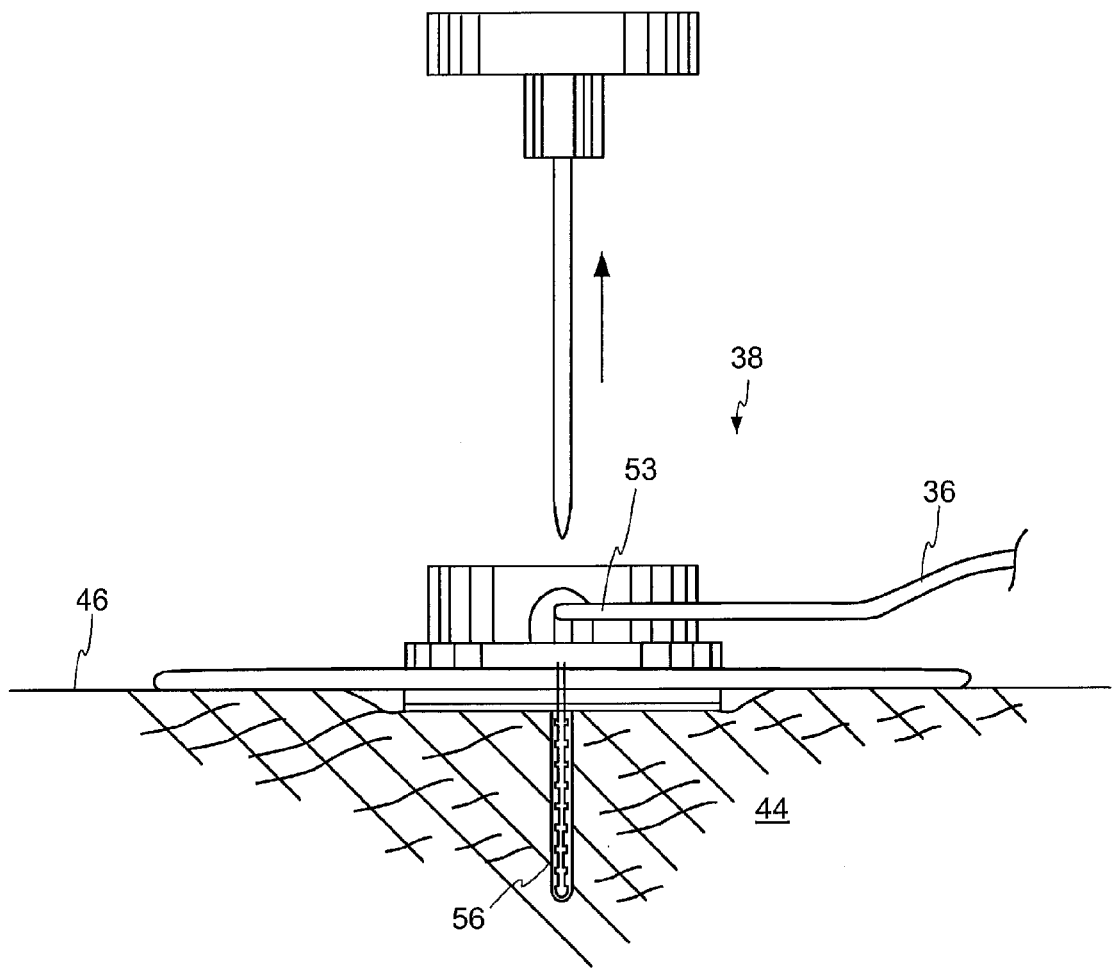
FIG. 6 is a side view of an example infusion set with an insertion needle pulled out, for use according to an embodiment.

FIGS. 2-6 illustrate example glucose control systems in accordance with certain embodiments. FIG. 2 is a front view of example closed loop hardware located on a body in accordance with certain embodiments. FIGS. 3(a)-3(d) and 4 show different views and portions of an example glucose sensor system for use in accordance with certain embodiments. FIG. 5 is a top view of an example infusion device with a reservoir door in an open position in accordance with certain embodiments. FIG. 6 is a side view of an example infusion set with an insertion needle pulled out in accordance with certain embodiments.

Particular example embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3(a) and 3(b), telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 3(d) and 4. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 3(c) and 3(d). Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 2 and 5 (and FIG. 1), a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucose may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 2 and 6). With reference to FIG. 6 (and FIG. 1), insulin 24 (e.g., of FIG. 1) may be forced through infusion tube 36 into infusion set 38 and into body 16 (e.g., of FIG. 1). Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 5) and subcutaneous tissue 44 of a user's body 16.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggybacks off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, anticoagulants, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 26, sensor set 28, telemetered characteristic monitor 30, sensor cable 32, infusion tube 36, infusion set 38, and so forth. Instead, standard blood glucose meters and/or vascular glucose sensors, such as those described in co-pending U.S. Patent Application Publication No. 2008/0221509 (U.S. patent application Ser. No. 12/121,647; to Gottlieb, Rebecca et al.; entitled "MULTILUMEN CATHETER"), filed May 15, 2008, may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Example System and/or Environmental Delays

Example system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that cause a sensor measurement to lag behind an actual present value. Also, as noted herein, such a delay may arise from, for instance, a particular level of noise filtering that is applied to a sensor signal.

Figure 7:
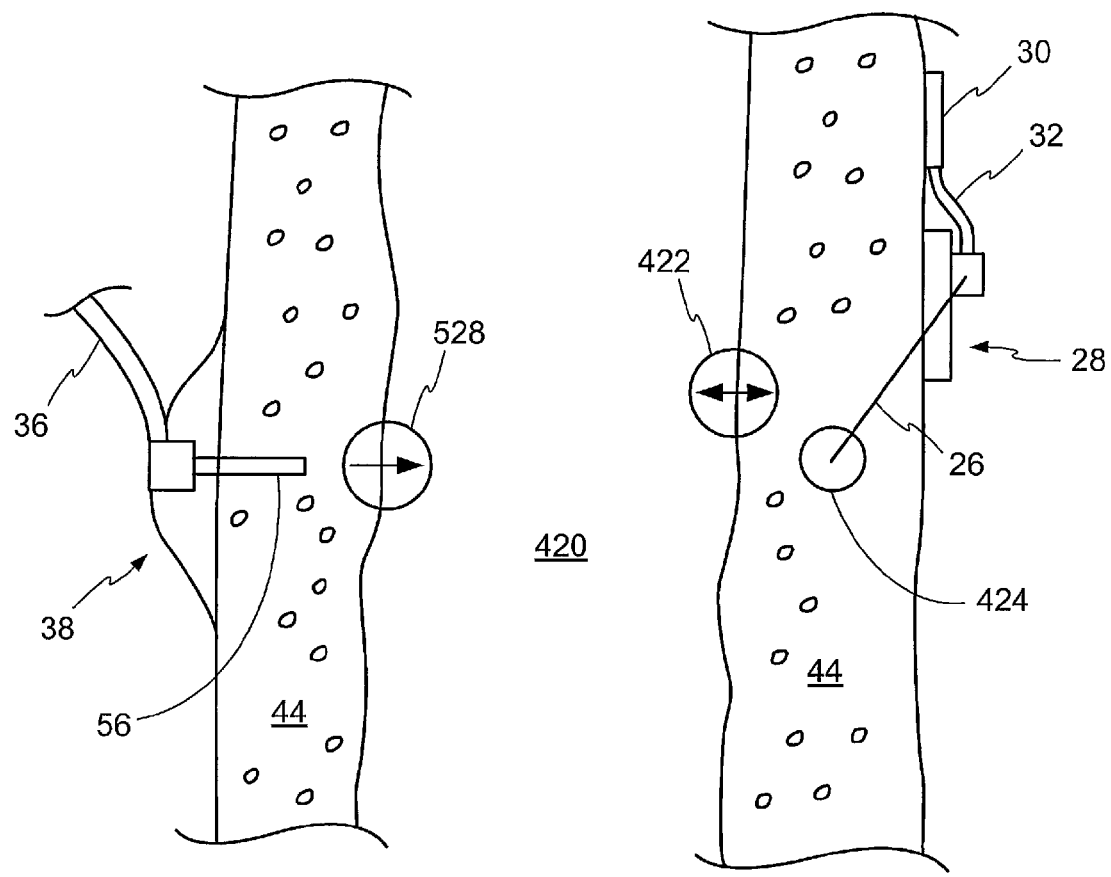
FIG. 7 is a cross-sectional view of an example sensor set and an example infusion set attached to a body in accordance with an embodiment.

FIG. 7 is a cross-sectional view of an example sensor set and an example infusion set that is attached to a body in accordance with an embodiment. In particular example implementations, as shown in FIG. 7, a physiological delay may arise from a time that transpires while glucose moves between blood plasma 420 and interstitial fluid (ISF). This example delay may be represented by a circled double-headed arrow 422. As discussed above with reference to FIG. 2-6, a sensor may be inserted into subcutaneous tissue 44 of body 20 such that electrode(s) 42 (e.g., of FIGS. 3 and 4) near a tip, or sending end 40, of sensor 26 are in contact with ISF. However, a parameter to be measured may include a concentration of glucose in blood.

Glucose may be carried throughout a body in blood plasma 420. Through a process of diffusion, glucose may move from blood plasma 420 into ISF of subcutaneous tissue 44 and vice versa. As blood glucose level 18 (e.g., of FIG. 1) changes, so does a glucose level of ISF. However, a glucose level of ISF may lag behind blood glucose level 18 due to a time required for a body to achieve glucose concentration equilibrium between blood plasma 420 and ISF. Some studies have shown that glucose lag times between blood plasma and ISF may vary between, e.g., 0 to 30 minutes. Some parameters that may affect such a glucose lag time between blood plasma and ISF are an individual's metabolism, a current blood glucose level, whether a glucose level is rising or falling, combinations thereof, and so forth, just to name a few examples.

A chemical reaction delay 424 may be introduced by sensor response times, as represented by a circle 424 that surrounds a tip of sensor 26 in FIG. 7. Sensor electrodes 42 (e.g., of FIGS. 3 and 4) may be coated with protective membranes that keep electrodes 42 wetted with ISF, attenuate the glucose concentration, and reduce glucose concentration fluctuations on an electrode surface. As glucose levels change, such protective membranes may slow the rate of glucose exchange between ISF and an electrode surface. In addition, there may be chemical reaction delay(s) due to a reaction time for glucose to react with glucose oxidase GOX to generate hydrogen peroxide and a reaction time for a secondary reaction, such as a reduction of hydrogen peroxide to water, oxygen, and free electrons.

Thus, an insulin delivery delay may be caused by a diffusion delay, which may be a time for insulin that has been infused into a tissue to diffuse into the blood stream. Other contributors to insulin delivery delay may include, but are not limited to: a time for a delivery system to deliver insulin to a body after receiving a command to infuse insulin; a time for insulin to spread throughout a circulatory system once it has entered the blood stream; and/or by other mechanical, electrical/electronic, or physiological causes alone or in combination, just to name a few examples. In addition, a body clears insulin even while an insulin dose is being delivered from an insulin delivery system into the body. Because insulin is continuously cleared from blood plasma by a body, an insulin dose that is delivered to blood plasma too slowly or is delayed is at least partially, and possibly significantly, cleared before the entire insulin dose fully reaches blood plasma. Therefore, an insulin concentration profile in blood plasma may never achieve a given peak (nor follow a given profile) that it may have achieved if there were no delay.

Moreover, there may also be a processing delay as an analog sensor signal Isig is converted to digital sensor values Dsig. In particular example embodiments, an analog sensor signal Isig may be integrated over one-minute intervals and converted to a number of counts. Thus, in such a case, an analog-to-digital (A/D) conversion time may result in an average delay of 30 seconds. In particular example embodiments, one-minute values may be averaged into 5-minute values before they are provided to controller 12 (e.g., of FIG. 1). A resulting average delay may be two-and-one-half minutes (e.g., half of the averaging interval). In example alternative embodiments, longer or shorter integration times may be used that result in longer or shorter delay times.

In other example embodiments, an analog sensor signal current Isig may be continuously converted to an analog voltage Vsig, and an A/D converter may sample voltage Vsig every 10 seconds. Thus, in such a case, six 10-second values may be pre-filtered and averaged to create a one-minute value. Also, five one-minute values may be filtered and averaged to create a five-minute value that results in an average delay of two-and-one-half minutes. In other alternative embodiments, other sensor signals from other types of sensors may be converted to digital sensor values Dsig as appropriate before transmitting the digital sensor values Dsig to another device. Moreover, other embodiments may use other electrical components, other sampling rates, other conversions, other delay periods, a combination thereof, and so forth.

System Configuration Examples

FIG. 8(a)-8(d) illustrate example diagrams of one or more devices and their components for glucose control systems in accordance with certain embodiments. These FIG. 8(a)-8(d) show exemplary, but not limiting, illustrations of components that may be utilized with certain controller(s) that are described herein above. Various changes in components, layouts of such components, combinations of elements, and so forth may be made without departing from the scope of claimed subject matter.

Before it is provided as an input to controller 12 (e.g., of FIG. 1), a sensor signal 16 may be subjected to signal conditioning such as pre-filtering, filtering, calibrating, and so forth, just to name a few examples. Components such as a pre-filter, one or more filters, a calibrator, controller 12, etc. may be separately partitioned or physically located together (e.g., as shown in FIG. 8(a)), and they may be included with a telemetered characteristic monitor transmitter 30, an infusion device 34, a supplemental device, and so forth.

Figure 8:
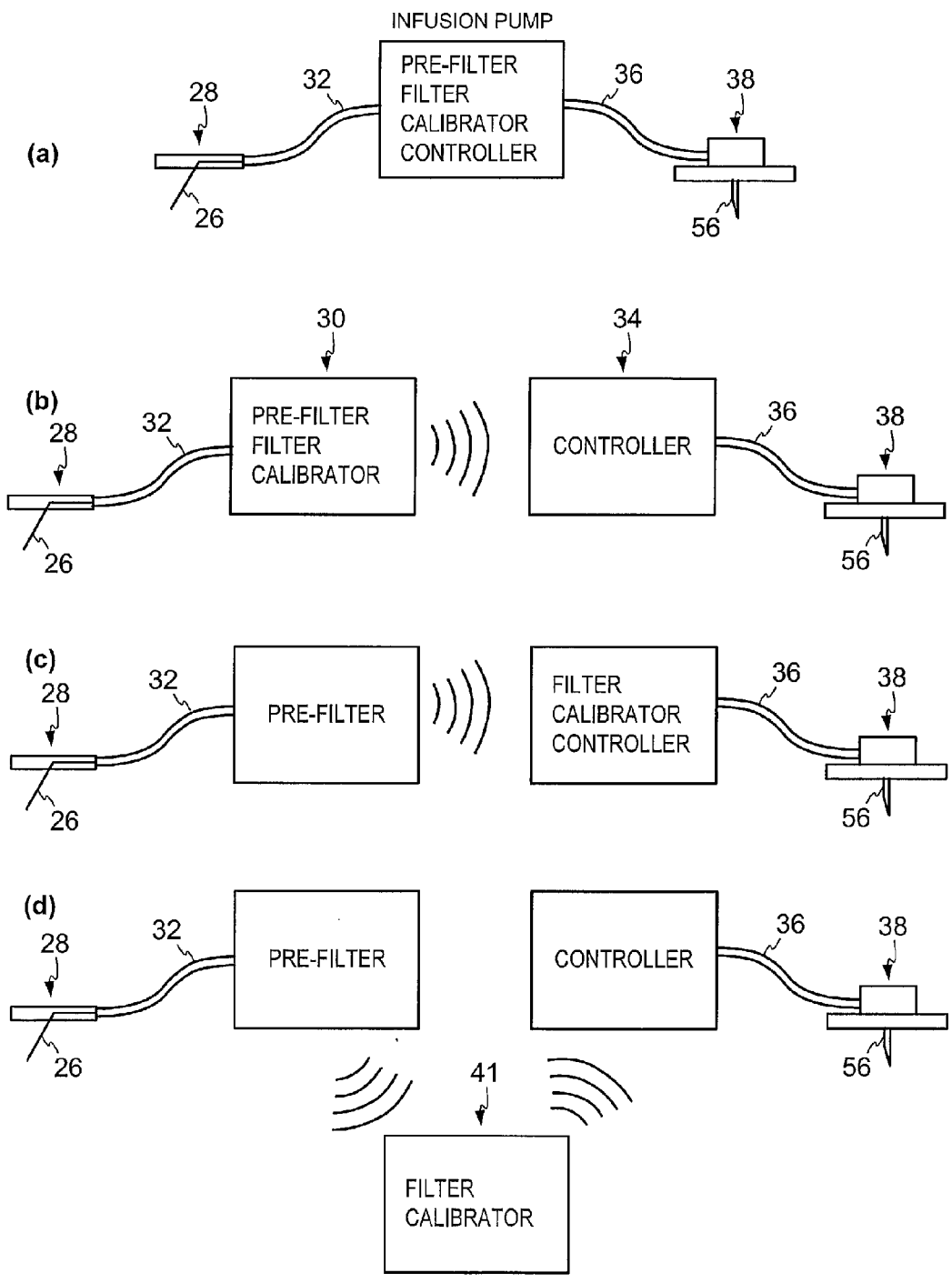
FIG. 8(a) is a diagram of an example single device and its components for a glucose control system in accordance with an embodiment.
FIG. 8(b) is a diagram of two example devices and their components for a glucose control system in accordance with an embodiment.
FIG. 8(c) is another diagram of two example devices and their components for a glucose control system in accordance with an embodiment.
FIG. 8(d) is a diagram of three example devices and their components for a glucose control system in accordance with an embodiment.

In particular example embodiments, a pre-filter, filter(s), and a calibrator may be included as part of telemetered characteristic monitor transmitter 30, and a controller (e.g., controller 12) may be included with infusion device 34, as shown in FIG. 8(b). In example alternative embodiments, a pre-filter may be included with telemetered characteristic monitor transmitter 30, and a filter and calibrator may be included with a controller in an infusion device, as shown in FIG. 8(c). In other alternative example embodiments, a pre-filter may be included with telemetered characteristic monitor transmitter 30, while filter(s) and a calibrator are included in supplemental device 41, and a controller may be included in the infusion device, as shown in FIG. 8(*d*).

In particular example embodiments, a sensor system may generate a message that includes information based on a sensor signal such as digital sensor values, pre-filtered digital sensor values, filtered digital sensor values, calibrated digital sensor values, commands, and so forth, just to name a few examples. Such a message may include other types of information as well, including, by way of example but not limitation, a serial number, an ID code, a check value, values for other sensed parameters, diagnostic signals, other signals, and so forth. In particular example embodiments, digital sensor values Dsig may be filtered in a telemetered characteristic monitor transmitter 30, and filtered digital sensor values may be included in a message sent to infusion device 34 where the filtered digital sensor values may be calibrated and used in a controller. In other example embodiments, digital sensor values Dsig may be filtered and calibrated before transmission to a controller in infusion device 34. Alternatively, digital sensor values Dsig may be filtered, calibrated, and used in a controller to generate commands 22 that are sent from telemetered characteristic monitor transmitter 30 to infusion device 34.

In further example embodiments, additional components, such as a post-calibration filter, a display, a recorder, a blood glucose meter, etc. may be included in devices with any of the other components, or they may stand-alone. If a blood glucose meter is built into a device, for instance, it may be co-located in the same device that contains a calibrator. In alternative example embodiments, more, fewer, and/or different components may be implemented than those that are shown in FIG. 8 and/or described herein above.

In particular example embodiments, RF telemetry may be used to communicate between devices that contain one or more components, such as telemetered characteristic monitor transmitter 30 and infusion device 34. In alternative example embodiments, other communication mediums may be employed between devices, such as wireless wide area network (WAN) (e.g., cell communication), Wi-Fi, wires, cables, IR signals, laser signals, fiber optics, ultrasonic signals, and so forth, just to name a few examples.

FIG. 9 is a schematic diagram of an example closed loop system 900 to control blood glucose levels via insulin infusion and/or glucagon infusion using at least a controller based on glucose level feedback via a sensor signal in accordance with an embodiment. In particular example embodiments, a closed loop control system may be used for delivering insulin to a body to compensate for β-cells that perform inadequately. There may be a desired basal blood glucose level $G_B$ for a particular body. A difference between a desired basal blood glucose level $G_B$ and an estimate of a present blood glucose level G is the glucose level error $G_E$ that may be corrected. For particular example embodiments, glucose level error $G_E$ may be provided as an input to controller 12, as shown in FIG. 9. Although at least a portion of controller 12 may be realized as a proportional-integral-derivative (PID) controller, claimed subject matter is not so limited, and controller 12 may be realized in alternative manners.

If glucose level error $G_E$ is positive (meaning, e.g., that a present estimate of blood glucose level G is higher than a desired basal blood glucose level $G_B$), then a command from controller 12 may generate a command 22 to drive insulin delivery system 34 to provide insulin 24 to body 20. Insulin delivery system 34 may be an example implementation of insulin delivery system 14 (e.g., of FIG. 1). Likewise, if $G_E$ is negative (meaning, e.g., that a present estimate of blood glucose level G is lower than a desired basal blood glucose level $G_B$), then a command from controller 12 may generate a command 22 to drive glucagon delivery system 35 to provide glucagon 25 to body 20. Glucagon delivery system 35 may be an example implementation of glucagon delivery system 15 (e.g., of FIG. 1).

Closed loop system 900 may also include and/or be in communication with a human interface 65. Example implementations for a human interface 65 are described herein above with particular reference to FIG. 1 in the context of an output device. As shown, human interface 65 may receive one or more commands 22 from controller 12. Such commands 22 may include, by way of example but not limitation, one or more commands to communicate information to a user (e.g., a patient, a healthcare provider, etc.) visually, audibly, haptically, some combination thereof, and so forth. Such information may include data, an alert, or some other notification 55. Human interface 65 may include a screen, a speaker, a vibration mechanism, any combination thereof, and so forth, just to name a few examples. Hence, in response to receiving a command 22 from controller 12, human interface 65 may present at least one notification 55 to a user via a screen, a speaker, a vibration, and so forth.

In terms of a control loop for purposes of discussion, glucose may be considered to be positive, and therefore insulin may be considered to be negative. Sensor 26 may sense an ISF glucose level of body 20 and generate a sensor signal 16. For certain example embodiments, a control loop may include a filter and/or calibration unit 456 and/or correction algorithm(s) 454. However, this is by way of example only, and claimed subject matter is not so limited. Sensor signal 16 may be filtered/or and calibrated at unit 456 to create an estimate of present blood glucose level 452. Although shown separately, filter and/or calibration unit 456 may be integrated with controller 12 without departing from claimed subject matter. Moreover, filter and/or calibration unit 456 may alternatively be realized as part of controller 12 (or vice versa) without departing from claimed subject matter.

In particular example embodiments, an estimate of present blood glucose level G may be adjusted with correction algorithms 454 before it is compared with a desired basal blood glucose level $G_B$ to calculate a new glucose level error $G_E$ to start a loop again. Also, an attendant, a caretaker, a patient, etc. may obtain blood glucose reference sample measurements from a patient's blood using, e.g., glucose test strips. These blood-based sample measurements may be used to calibrate ISF-based sensor measurements, e.g. using techniques such as those described in U.S. Pat. No. 6,895,263, issued May 17, 2005, and/or other techniques. Although shown separately, a correction algorithms unit 454 may be integrated with controller 12 without departing from claimed subject matter. Moreover, correction algorithms unit 454 may alternatively be realized as part of controller 12 (or vice versa) without departing from claimed subject matter. Similarly, a difference unit and/or other functionality for calculating $G_E$ from G and $G_B$ may be incorporated as part of controller 12 without departing from claimed subject matter.

For an example PID-type of controller 12, if a glucose level error $G_E$ is negative (meaning, e.g., that a present estimate of blood glucose level is lower than a desired basal blood glucose level $G_B$), then controller 12 may reduce or stop insulin delivery depending on whether an integral component response of a glucose error $G_E$ is still positive. In alternative embodiments, as discussed below, controller 12 may initiate infusion of glucagon 25 if glucose level error $G_E$ is negative. If a glucose level error $G_E$ is zero (meaning, e.g., that a present estimate of blood glucose level is equal to a desired basal blood glucose level $G_B$), then controller 12 may or may not issue commands to infuse insulin 24 or glucagon 25, depending on a derivative component (e.g., whether a glucose level is rising or falling) and/or an integral component (e.g., how long and by how much a glucose level has been above or below basal blood glucose level $G_B$).

To more clearly understand the effects that a body has on such a control loop, a more detailed description of example physiological effects that insulin may have on glucose concentration in ISF is provided. In particular example embodiments, infusion delivery system 34 may deliver insulin into ISF of subcutaneous tissue 44 (e.g., also of FIGS. 3, 4, and 6) of body 20. Alternatively, insulin delivery system 34 or a separate infusion device (e.g., glucagon delivery system 35) may similarly deliver glucose and/or glucagon into ISF of subcutaneous tissue 44. Here, insulin 24 may diffuse from local ISF surrounding a cannula into blood plasma and spread throughout body 20 in a main circulatory system (e.g., as represented by blood stream 47). Infused insulin may diffuse from blood plasma into ISF substantially throughout the entire body.

Here in the body, insulin 24 may bind with and activate membrane receptor proteins on cells of body tissues. This may facilitate glucose permeation into activated cells. In this way, tissues of body 20 may take up glucose from ISF. As ISF glucose level decreases, glucose may diffuse from blood plasma into ISF to maintain glucose concentration equilibrium. Glucose in ISF may permeate a sensor membrane of sensor 26 and affect sensor signal 16.

In addition, insulin may have direct and indirect effects on liver glucose production. Typically, increased insulin concentration may decrease liver glucose production. Therefore, acute and immediate insulin response may not only help a body to efficiently take up glucose, but it may also substantially stop a liver from adding to glucose in the blood stream. In alternative example embodiments, as pointed out above, insulin and/or glucose may be delivered more directly into the blood stream instead of into ISF, such as by delivery into veins, arteries, the peritoneal cavity, and so forth, just to name a few examples. Accordingly, any time delay associated with moving insulin and/or glucose from ISF into blood plasma may be diminished. In other alternative example embodiments, a glucose sensor may be in contact with blood or other body fluids instead of ISF, or a glucose sensor may be outside of a body such that it may measure glucose through a non-invasive means. Embodiments using alternative glucose sensors may have shorter or longer delays between an actual blood glucose level and a measured blood glucose level.

A continuous glucose measuring sensor (CGMS) implementation for sensor 26, for example, may detect a glucose concentration in ISF and provide a proportional current signal. A current signal (Isig) may be linearly correlated with a reference blood glucose concentration (BG). Hence, a linear model, with two parameters (e.g., slope and offset), may be used to calculate a sensor glucose concentration (SG) from sensor current Isig.

One or more controller gains may be selected so that commands from a controller 12 direct infusion device 34 to release insulin 24 into body 20 at a particular rate. Such a particular rate may cause insulin concentration in blood to follow a similar concentration profile as would be caused by fully functioning human β-cells responding to blood glucose concentrations in a body. Similarly, controller gain(s) may be selected so that commands 22 from controller 12 direct an infusion device of glucagon delivery system 35 to release glucagon 25 in response to insulin excursions. In particular example embodiments, controller gains may be selected at least partially by observing insulin response(s) of several normal glucose tolerant (NGT) individuals having healthy, normally-functioning β-cells.

In one or more example implementations, a system may additionally include a communication unit 458. A communication unit 458 may comprise, by way of example but not limitation, a wireless wide area communication module (e.g., a cell modem), a transmitter and/or a receiver (e.g., a transceiver), a Wi-Fi or Bluetooth chip or radio, some combination thereof, and so forth. Communication unit 458 may receive signals from, by way of example but not limitation, filter and/or calibration unit 456, sensor 26 (e.g., sensor signal 16), controller 12 (e.g. commands 22), any combination thereof, and so forth. Although not specifically shown in FIG. 9, communication unit 458 may also receive signals from other units (e.g., correction algorithms unit 454, a delivery system 34 and/or 35, human interface 65, etc.). Also, communication unit 458 may be capable of providing signals to any of the other units of FIG. 9 (e.g., controller 12, filter and/or calibration unit 456, human interface 65, etc.). Communication unit 458 may also be integrated with or otherwise form a part of another unit, such as controller 12 or filter and/or calibration unit 456.

Communication unit 458 may be capable of transmitting calibration output; calibration failure alarms; control algorithm states; sensor signal alerts; and/or other physiological, hardware, and/or software data (e.g., diagnostic data); and so forth to a remote data center for additional processing and/or storage (e.g., for remote telemetry purposes). These transmissions can be performed in response to discovered/detected conditions, automatically, semi-automatically (e.g., at the request of the remote data center), manually at the request of the patient, any combination thereof, and so forth, just to provide a few examples. The data can be subsequently served on request to remote clients including, but not limited to, mobile phones, physician's workstations, patient's desktop computers, any combination of the above, and so forth, just to name a few examples. Communication unit 458 may also be capable of receiving from a remote location various information, including but not limited to: calibration information, instructions, operative parameters, other control information, some combination thereof, and so forth. Such control information may be provided from communication unit 458 to other system unit(s) (e.g., controller 12, filter and/or calibration unit 456, etc.).

As pointed out above, in certain example implementations a continuous glucose monitoring sensor may measure glucose concentration in ISF by oxidizing localized glucose with the help of a glucose-oxidizing enzyme. A sensor output signal may comprise a current signal (Isig, nAmps) which may be at least roughly an increasing function of a glucose concentration in ISF. Under particular conditions (e.g., accumulation of contaminants, etc.), a sensor's sensitivity in responding to a blood glucose concentration may diminish with normal use over time. Eventually, a sensitivity of a glucose sensor may diminish to a point where the sensor becomes unreliable and should be replaced.

Figure 10:
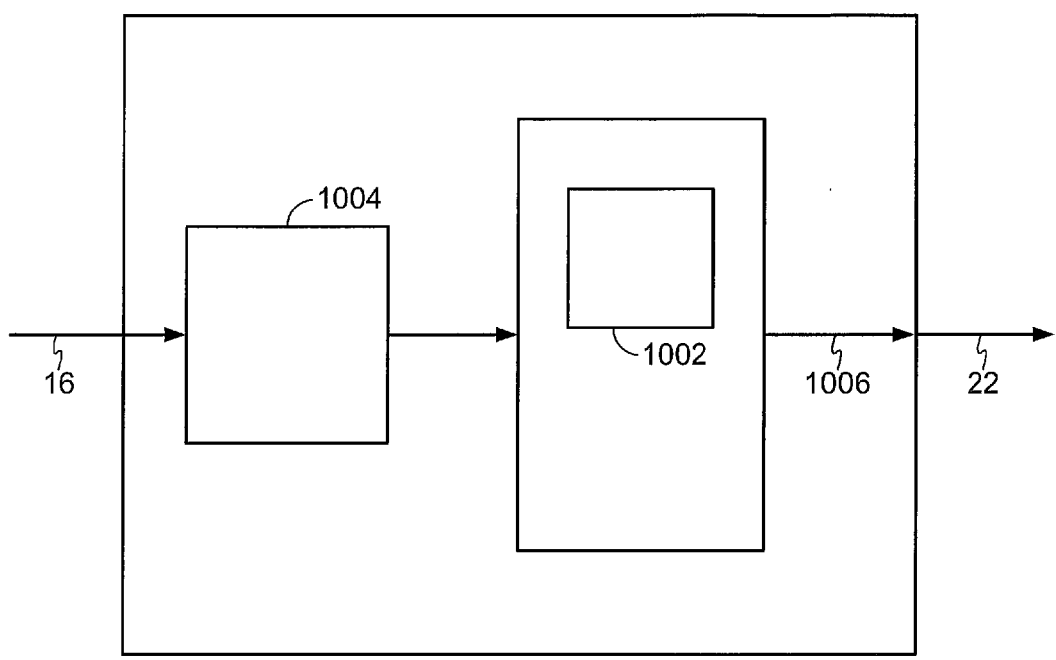
FIG. 10 is a schematic diagram of at least a portion of an example controller including a sensor sensitivity analyzer in accordance with an embodiment.

FIG. 10 is a schematic diagram of at least a portion of an example controller 12 including a sensor signal reliability analyzer 1002. As illustrated, controller 12 may include a sensor sensitivity analyzer 1002, and controller 12 may include or have access to a series of samples 1004 and may produce at least one alert signal 1006.

For certain example embodiments, series of samples 1004 may comprise multiple samples taken from a sensor signal 16 (e.g., also of FIGS. 1 and 9) at multiple sampling times. Thus, series of samples 1004 may include multiple samples of at least one sensor signal, such as sensor signal 16, and may be responsive to a blood glucose level of a patient.

Sensor sensitivity analyzer 1002 may consider one or more facets of series of samples 1004 to assess sensor sensitivity in responding to a presence of glucose in blood or interstitial fluid. Based at least partly on such assessment(s), sensor sensitivity analyzer 1002 may produce at least one alert signal 1006. In one embodiment, an alert signal 1006 may be issued in response to an assessment indicating that a sensor signal may not be sufficiently reliable (e.g., sufficiently sensitive in responding to a presence of glucose in blood or interstitial fluid) so as to justify entrusting a patient's health to closed-loop glucose control decisions that are based on such an unreliable sensor signal. Such an indication may be responsive to, for example, an indication that a sensitivity of a sensor to the presence of glucose in bodily fluid has degraded significantly. In example implementations, an alert signal 1006 may comprise at least one command 22 (e.g., also of FIGS. 1 and 9) that is issued from controller 12. For instance, an alert signal 1006 may be provided to a human interface 65 (e.g., of FIG. 9) and/or an insulin delivery system 34 (e.g., of FIG. 9). Alternatively and/or additionally, an alert signal 1006 may be provided to another component and/or unit of (e.g., that is internal of) controller 12.

Figure 11:
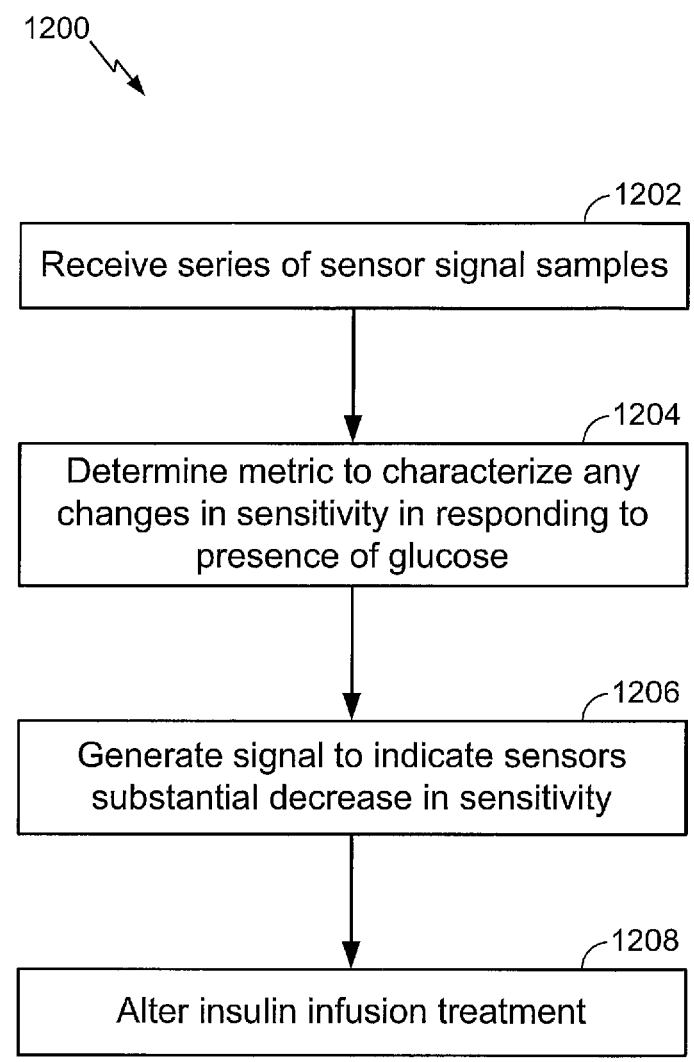
FIG. 11 is a flow diagram of an example process for detecting sensor sensitivity drift in accordance with an embodiment.

FIG. 11 is a flow diagram 1200 of an example method for assessing operation of a glucose sensor in accordance with an embodiment. Although operations 1202-1208 are shown and described in a particular order, it should be understood that methods may be performed in alternative orders and/or manners (including with a different number of operations) without departing from claimed subject matter. At least some operation(s) of flow diagram 1200 may be performed so as to be fully or partially overlapping with other operation(s). Additionally, although the description below may reference particular aspects and features illustrated in certain other figures, methods may be performed with other aspects and/or features.

For certain example implementations, at operation 1202, a series of samples of at least one sensor signal that is responsive to a blood glucose level of a patient may be obtained. At operation 1204, at least one sensitivity metric may be determined, based at least partly on the series of samples of the at least one sensor signal, to characterize changes in sensitivity in responding to the presence of glucose in a bodily fluid such as blood. Here, in a particular implementation, and as explained below, such a sensitivity metric may be computed based, at least in part, on a measured or estimated dispersion of a rate of change of sensor signal measurements with respect to time (e.g., a first derivative of Isig dIsig/dt being just one non-limiting example of a rate of change in sensor signal measurements) over a time period. Another sensitivity metric may be determined based, at least in part on a mean value for Isig over such a time period.

At operation 1206, an alert signal may be generated responsive to a comparison of the at least one sensitivity metric with at least one predetermined threshold. For example, a measured or estimated dispersion of dIsig/dt may be compared with a first threshold and/or a mean value for Isig may be compared with a second threshold. Alternatively, a weighted (e.g., time-weighted) average of Isig may be compared with such a threshold. Use of a time-weighted average may allow for use of longer windows while still emphasizing more recent measurements. Here, weighting may be applied in a single-tailed fashion, where the more recent data is weighted more heavily than older data within a particular window. Particular weighting functions may include, for example, an exponential decay or one-sided Gaussian distribution. Particular conditions that may be indicative of a sensor's decreased sensitivity in responding to the presence of glucose are as discussed above. In an example implementation, an alert may be generated by initiating a signal to indicate to a blood glucose controller that the sensor's sensitivity to a presence of glucose may have decreased substantially.

At operation 1208, an insulin infusion treatment for the patient may be altered responsive at least partly to the assessed reliability of the at least one sensor signal. For example, an insulin infusion treatment for a patient may be altered by changing (e.g., increasing or decreasing) an amount of insulin being infused, by ceasing an infusion of insulin, by delaying infusion until more samples are taken, by switching to a different sensor, by switching to a manual mode, by changing a relative weighting applied to a given sensor or sensors and/or the samples acquired there from, any combination thereof, and so forth, just to name a few examples.

Figure 12:
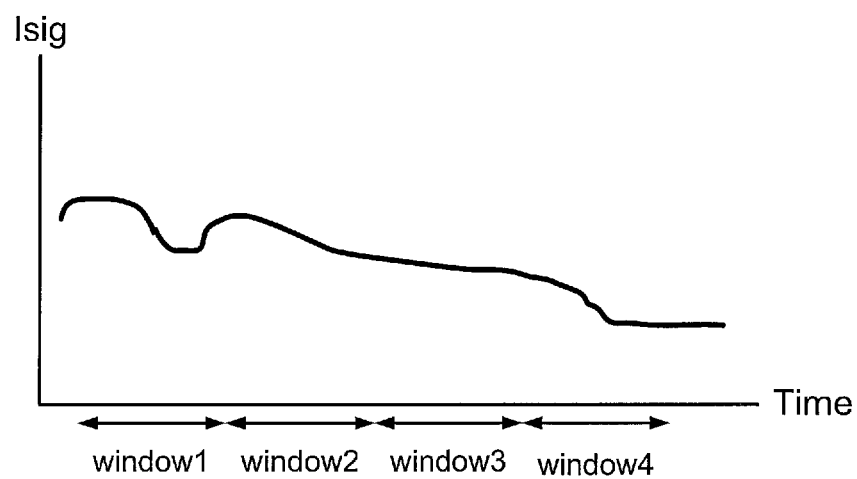
FIG. 12 is a plot illustrating a change in sensitivity of a blood glucose sensor according to an embodiment.
Figure 13:
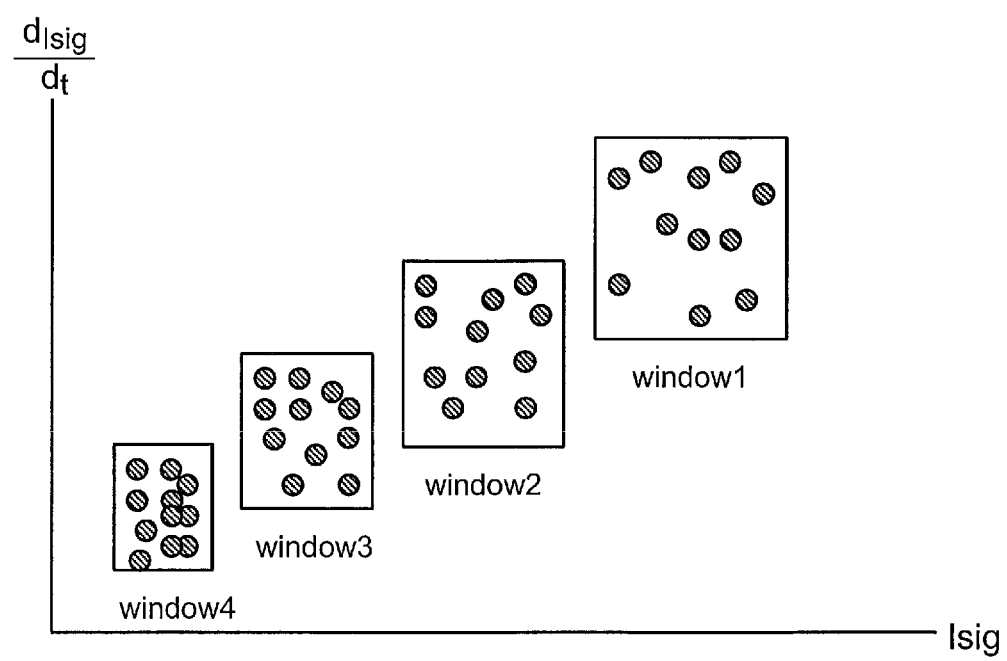
FIG. 13 is a plot of an estimated first derivative of a sensor signal sample as a function of signal sample amplitude and aggregated in distinct time intervals.
Figure 14:
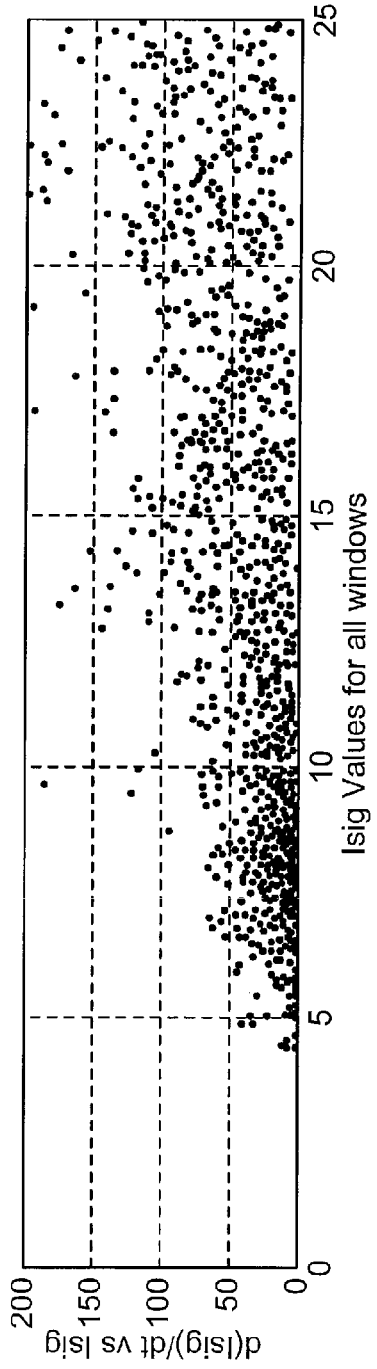
FIG. 14 is a plot of a first derivative of sensor measurement values as a function of sensor measurement values according to an embodiment.
Figure 15:
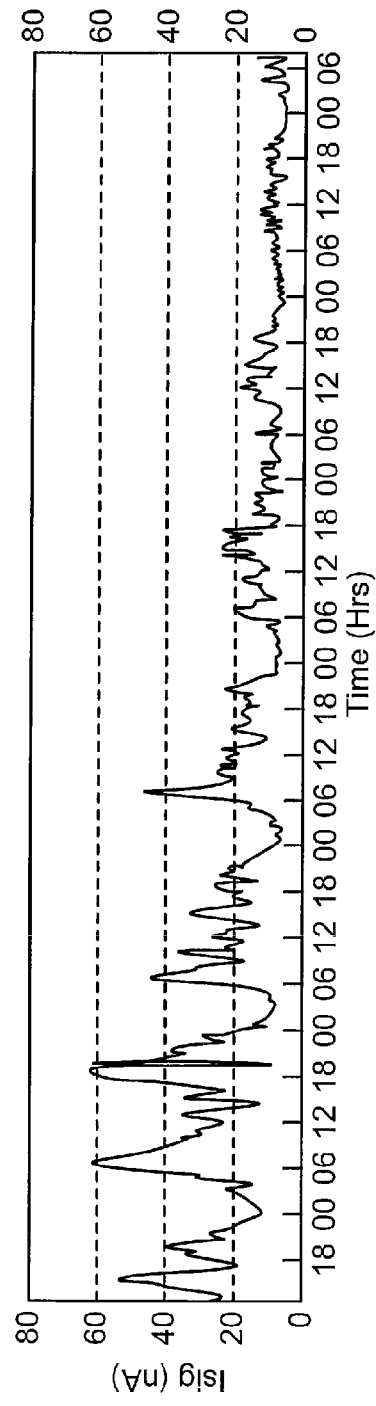
FIGS. 15 and 16 are plots of sensor measurement values taken over time and corresponding blood glucose concentration levels according to an embodiment.
Figure 16:
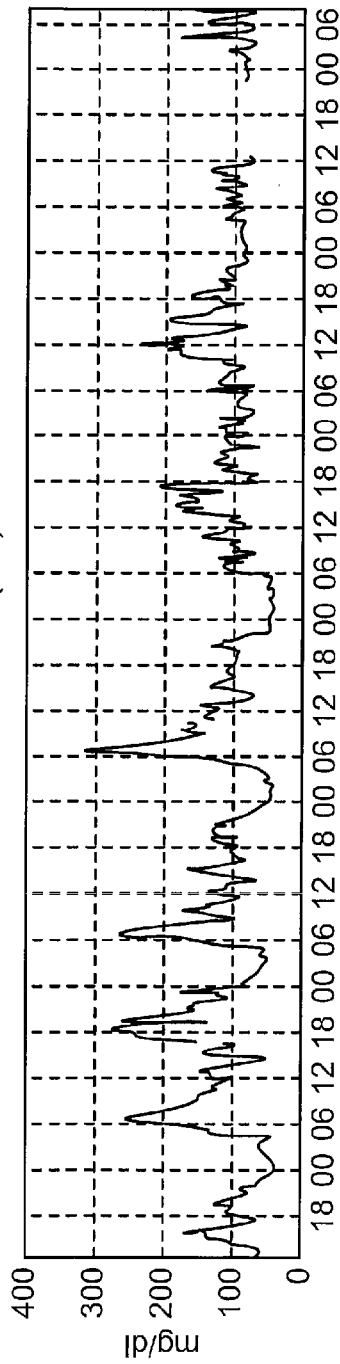

As discussed above, Isig may represent current measurements which are reflective of a blood glucose concentration. FIG. 15 plots the behavior of Isig in a patient over a time period spanning several days for blood glucose concentration levels shown in FIG. 16. As can be observed, a range from troughs to peaks decreases over time, indicating a decreased sensitivity in responsiveness to a presence of blood glucose. FIG. 14 is a plot of dIsig/dt for discrete Isig values in FIG. 15. A decreased sensitivity in a glucose sensor in responding to a presence of glucose may be more clearly illustrated in FIGS. 12 and 13. Here, FIG. 12 is a plot illustrating a change in sensitivity of a glucose sensor to the presence of glucose in a fluid over a sequence of time windows. As shown in the particular example of FIG. 12, an amplitude of Isig may trend lower over time due to a decreased sensitivity of a sensor to the presence of glucose in fluid. In a particular implementation, a sensitivity of a sensor to the presence of glucose may decrease to the point where Isig values are no longer reliable for certain applications such as providing reliable estimates or predictions of blood glucose in a closed-loop insulin delivery system.

As pointed out above, FIG. 12 shows a segmentation of operation time into distinct "windows" during which Isig values may be processed for evaluating a sensitivity of a sensor in responding to the presence of glucose in fluid (e.g., at operation 1204). As discussed below, Isig values obtained in any particular window may be evaluated to determine whether the sensor's sensitivity to the presence of glucose has decreased to the point that action is to be taken (e.g., at operation 1206). In the particular embodiment of FIG. 12, such an evaluation of Isig values may performed at each non-overlapping window as shown. Alternatively, implementation, a window for capturing Isig values for evaluation may comprise a sliding window. Here, the size of the window may be set so as to balance responsiveness to changes in sensitivity and accuracy (e.g., by having a large number of data points. For example, if a window size is too large, a detection of a loss of sensitivity may be unnecessarily delayed resulting in a delayed alarm to the user. On the other hand, if the window size is too small, a detection scheme may be overly sensitive, resulting in false alarms. In one implementation, a window size may be a particular meal period (e.g., ⅓ of the day assuming three meals in a 24-hour period). A window size may also be set by an algorithm subject to an amount of time likely to reach particular threshold conditions (e.g., value for Isig). A window size may also be set according to a patient-specific meal cycle (e.g., from historical data) where the window is to be long enough to capture a patient's glucose highs and lows throughout the day. For example, if a window is set at a very short period (e.g., 1.0 hour), hitting only highs or only lows may trigger false alarms. A long-term running-window covering several meal periods (e.g., one day) may be effective at measuring an estimated dispersion of Isig/dt. Also, time windows for a particular time of day on one day may be compared with the same time of day on a different day to detecting a change in sensitivity. FIG. 13 is a plot of an estimated first derivative of a sensor signal sample as a function of signal sample amplitude and aggregated in distinct time intervals corresponding to window1 through window4 shown in FIG. 12. As can be observed by inspection, Isig values obtained at the earliest window1 tend to be at the highest levels. Also, dIsig/dt for Isig values obtained at window1 show the greatest degree of dispersion, indicating a high sensitivity in responding to the presence of glucose. In contrast, dIsig/dt determined for Isig values obtained at window4 show the smallest degree of dispersion, indicating a diminished sensitivity in responding to a presence of glucose.

In one particular implementation, for any particular window of Isig measurements, a sensitivity metric (e.g., dispersion of dIsig/dt and/or mean value for Isig) may be computed (e.g., at operation 1204) and compared to a threshold (e.g. at operation 1206) for determining whether action should be taken.

Here, in a particular implementation, if the sensitivity metric falls below a threshold level, indicating a reduced sensor sensitivity in responding to the presence of blood glucose, one or more actions may be taken as discussed above. In a particular implementation, multiple sensitivity metrics may be derived (e.g., dispersion of dIsig/dt and/or mean value for Isig) and different combinations of conditions may be tested at operation 1206. For example, a signal indicating a substantial decrease in sensitivity may be initiated in response to a combination of both a dispersion of Isig/dt being less than a first threshold and mean value for Isig being less than a second threshold. In the particular implementation described above, a variance of dIsig/dt is used an indicator or measurement of a dispersion of Isig/dt. While the above example uses a variance of dIsig/dt is used an indicator or measurement of a dispersion of Isig/dt, other metrics may be used such as a coefficient of variation, root mean of the squared error (RMSE), normalized RMSE or sum of the squared errors (SSE). It should be understood, however, that these are merely examples of how a dispersion of dIsig/dt, either a statistical dispersion or otherwise, may be quantified according to a particular implementation, and that claimed subject matter is not limited in this respect.

A value for dIsig/dt may be computed using any one of several techniques. Techniques for determining or estimating dIsig/dt provided herein are merely example techniques, and it should be understood that any of these techniques mentioned, or techniques not mentioned, may be used without deviating from claimed subject matter. Applying a finite difference technique, a value for may be determined as follows:

$$dIsig(T)/dt = Isig(T) - Isig(T-k)]/(T-k),$$

where k is selected to filter noisy samples of Isig.

Applying a Savitzky-Golay filter, as discussed in Savitzky, A; Golay, MJE: Smoothing and differentiation of data by simplified least squares procedures, *Analytical Chemistry* 1964; 36 (8): 1627-1639, by performing a local polynomial regression of degree M on a series of values (e.g., of at least M+1 values equally spaced), Isig'(t) at discrete points may be computed as follows:

$$g_i = \sum_{n=i-N}^{i} c_n^M Isig_{i+n} \tag{7}$$

$$\frac{dIsig}{dt_i} = \frac{g_i}{\Delta}, \tag{8}$$

where:
N>M and values for c represent sample Savitzky-Golay coefficients.

In another particular implementation, Fourier decomposition may be used to compute a first derivative in the frequency domain as discussed in Jauberteau, F; Jauberteau, J L: Numerical differentiation with noisy signal, *Applied Mathematics and Computation* 2009; 215: 2283-2297. A piecewise cubic spline interpolation may be used smooth values for Isig(t). Its Fourier coefficients may give an approximation of Isig'(t).

Figure 17:
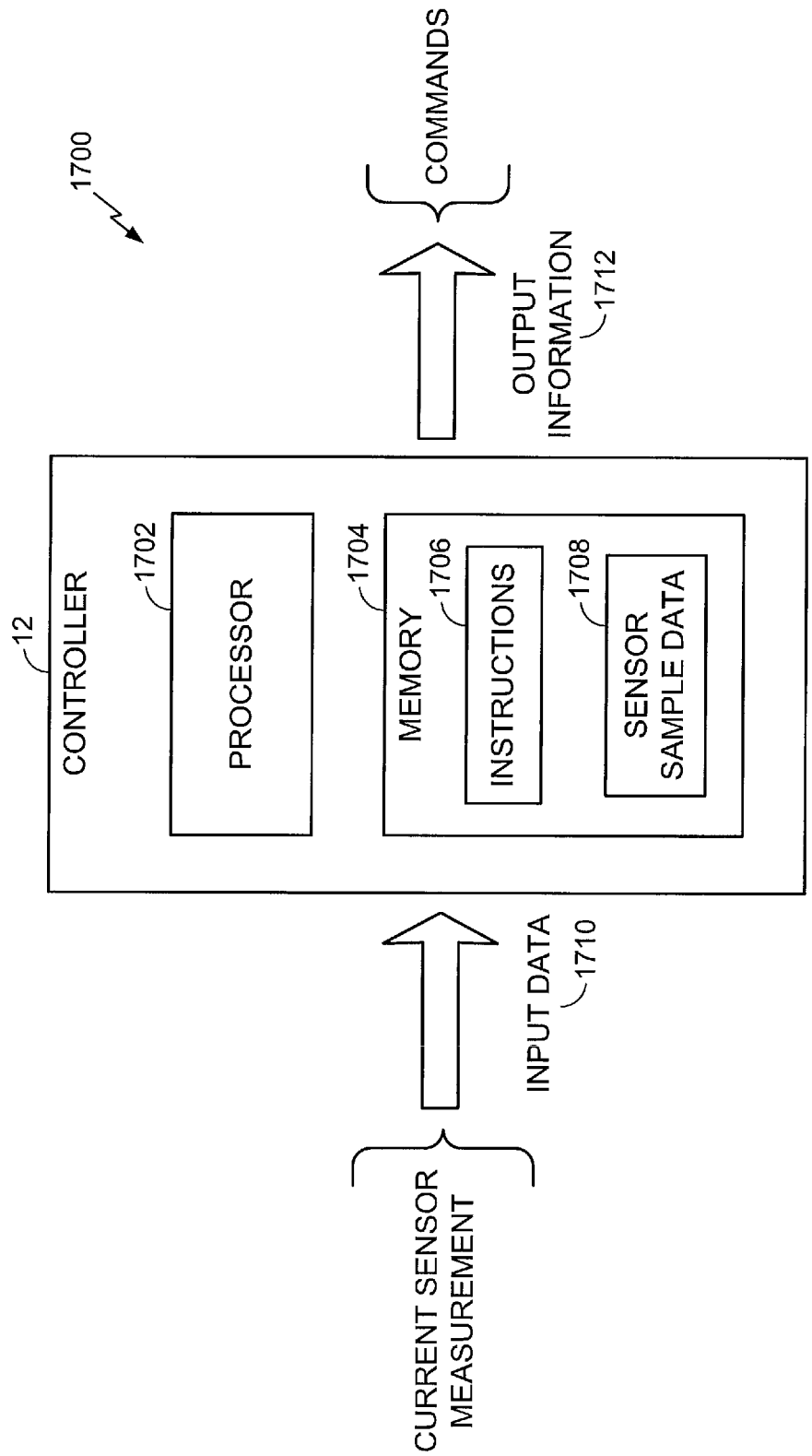
FIG. 17 is a schematic diagram of an example controller that produces output information based on input data in accordance with an embodiment.

FIG. 17 is a schematic diagram 1700 of an example controller 12 that produces output information 1712 based on input data 1710 in accordance with an embodiment. As illustrated, controller 12 may include one or more processors 1702 and at least one memory 1704. In certain example embodiments, memory 1704 may store or otherwise include instructions 1706 and/or sensor sample data 1708. Sensor sample data 1708 may include, by way of example but not limitation, blood glucose sensor measurements, such as series of samples 1004.

Input data 1710 may include, for example, sensor measurements (e.g., from an ISF current sensor). Output information 1712 may include, for example, one or more commands, and such commands may include reporting information. Current sensor measurements of input data 1710 may correspond to sensor signal 16 and/or sampled values resulting there from. Commands of output information 1712 may correspond to commands 22, which may be derived from one or more alert signals 1006 (e.g., of FIG. 10 and/or instructions or other information resulting there from.

In certain example embodiments, input data 1710 may be provided to controller 12. Based on input data 1710, controller 12 may produce output information 1712. Current sensor measurements that are received as input data 1710 may be stored as sensor sample data 1708. Controller 12 may be programmed with instructions 1706 to perform algorithms, functions, methods, etc.; to implement attributes, features, etc.; and so forth that are described herein. For example, a controller 12 may be configured to perform the functions described herein with regard to detecting a change in sensitivity of a sensor in responding to a presence of glucose in a fluid. Controller 12 may therefore be coupled to at least one blood glucose sensor to receive one or more signals based on blood glucose sensor measurements.

A controller 12 that comprises one or more processors 1702 may execute instructions 1706 to thereby render a controller unit a special purpose computing device to perform algorithms, functions, methods, etc.; to implement attributes, features, etc.; and so forth that are described herein. Processor(s) 1702 may be realized as microprocessors, digital signal processors (DSPs), application specific integrated circuits (ASICs), programmable logic devices (PLDs), controllers, micro-controllers, a combination thereof, and so forth, just to name a few examples. Alternatively, an article may comprise at least one storage medium (e.g., such as one or more memories) having stored thereon instructions 1706 that are executable by one or more processors.

Unless specifically stated otherwise, as is apparent from the preceding discussion, it is to be appreciated that throughout this specification discussions utilizing terms such as "processing", "computing", "calculating", "determining", "assessing", "estimating", "identifying", "obtaining", "representing", "receiving", "transmitting", "storing", "analyzing", "measuring", "detecting", "controlling", "delaying", "initiating", "providing", "performing", "generating", "altering" and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be understood that aspects described above are examples only and that embodiments may differ there from without departing from claimed subject matter. Also, it should be noted that although aspects of the above systems, methods, apparatuses, devices, processes, etc. have been described in particular orders and in particular arrangements, such specific orders and arrangements are merely examples and claimed subject matter is not limited to the orders and arrangements as described. It should additionally be noted that systems, devices, methods, apparatuses, processes, etc. described herein may be capable of being performed by one or more computing platforms.

In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although there have been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. An apparatus comprising:
   a glucose sensor to obtain measurements responsive to a presence of glucose in a fluid; and
   a processor to:
   detect a change in responsiveness of said glucose sensor to said presence of glucose in a fluid based, at least in part, on an application of one or more thresholds to one or more sensitivity metrics,
   at least one of said sensitivity metrics being computed based, at least part, on said measurements, wherein said change in responsiveness of said glucose sensor to the presence of glucose in said fluid is detected by:
   defining a sequence of windows in time;
   for at least one of said windows, computing a measure of dispersion of said rate of change; and
   determining at least one of said sensitivity metrics based, at least in part, on said computed measure of dispersion; wherein said at least one of said sensitivity metrics are detected by determining said at least one of said sensitivity metrics based, at least in part, on a ratio of said computed measure of dispersion and a mean value of glucose sensor measurements obtained in said at least one of said windows.

2. The apparatus of claim 1, wherein said change in responsiveness comprises a decrease in sensitivity of said glucose sensor to the presence of glucose in said fluid.

3. The apparatus of claim 1, wherein said computed measure of dispersion of said rate of change comprises a variance of said rate of change.

4. An article comprising:
   a non-transitory storage medium having machine-readable instructions stored thereon which are executable by a special purpose computing apparatus to:
   obtain a plurality of glucose sensor measurements at a glucose sensor over a time interval; and
   detect a change in responsiveness of said glucose sensor to a presence of glucose in a fluid based, at least in part, on an application of one or more thresholds to one or more sensitivity metrics, at least one of said sensitivity metrics being based, at least in part, on said glucose sensor measurements, wherein said change in responsiveness of said glucose sensor to the presence of glucose in said fluid is detected by:
   defining a sequence of windows in time;
   for at least one of said windows, computing a measure of dispersion of said rate of change; and
   determining at least one of said sensitivity metrics based, at least in part, on said computed measure of dispersion; wherein said at least one of said sensitivity metrics are detected by determining said at least one of said sensitivity metrics based, at least in part, on a ratio of said computed measure of dispersion and a mean value of glucose sensor measurements obtained in said at least one of said windows.

5. The article of claim 4, wherein said change in responsiveness comprises a decrease in sensitivity of said glucose sensor to the presence of glucose in said fluid.

6. The article of claim 4, wherein said computed dispersion of said rate of change comprises a variance of said rate of change.

7. An apparatus comprising:
means for obtaining a plurality of glucose sensor measurements at a glucose sensor over a time interval; and
means for detecting a change in responsiveness of said glucose sensor to a presence of glucose in a fluid based, at least in part, on an application of one or more thresholds to one or more sensitivity metrics, at least one of said sensitivity metrics being based, at least in part, on said glucose sensor measurements, wherein said means for detecting a change in responsiveness of said glucose sensor to the presence of glucose in said fluid detects said change in responsiveness by defining a sequence of windows in time; for at least one of said windows, computing a dispersion of said rate of change; and determining at least one of said sensitivity metrics based, at least in part, on said computed dispersion; wherein said at least one of said sensitivity metrics are detected by determining said at least one of said sensitivity metrics based, at least in part, on a ratio of said computed dispersion and a mean value of glucose sensor measurements obtained in said at least one of said windows.

* * * * *